United States Patent [19]

Smith et al.

[11] 4,294,923

[45] Oct. 13, 1981

[54] SUBSTRATES AND METHOD FOR DETERMINING ENZYMES

[76] Inventors: Robert E. Smith, 574 Escondido Cir., Livermore, Calif. 94550; Eugene R. Bissell, 101 Via Lucia, Alamo, Calif. 94507

[21] Appl. No.: 32,444

[22] Filed: Apr. 23, 1979

[51] Int. Cl.[3] .......................... C12Q 1/38; C12Q 1/36
[52] U.S. Cl. ...................................... 435/23; 435/24; 424/2; 424/7
[58] Field of Search ...................... 435/13, 23, 24, 805, 435/810; 424/2, 7

[56] References Cited

U.S. PATENT DOCUMENTS

| | | | |
|---|---|---|---|
| 4,056,519 | 11/1977 | Bobbitt et al. | 435/23 |
| 4,137,225 | 1/1979 | Enkenstam et al. | 435/23 |
| 4,147,692 | 4/1979 | Nagatsu et al. | 435/24 |
| 4,155,916 | 5/1979 | Smith et al. | 435/23 |
| 4,167,449 | 9/1979 | Garginlo et al. | 435/24 |
| 4,229,528 | 10/1980 | Smith et al. | 435/23 |

OTHER PUBLICATIONS

Zimmerman, et al., "A New Fluorgenic Substrate for Chymetypsin", *Anal. Biochem.*, vol. 70, No. 1 (1976), pp. 258–262.
Hammond, et al., "Search for Efficient, Near V. V. Lasing Dyes I, Substituent Effects on Bicyclic Dyes", *Appl. Phys.*, vol. 8, No. 4 (1975), pp. 311–314.
Hammond et al., "Search for Efficient, Nerve V. V. Lasing Dyes, II Aza Substitution in Bicylic Dyes", *Appl. Phys.*, vol. 8, No. 4 (1975), pp. 315–318.
Kosower *Physical Organic Chemistry*, John Wiley & Sons, Inc., New York (1968), pp. 38, 45, 47, 49.
Smith et al., "Direct Photometric or Flurometric Assay of Proteinases Using Substrates Containing 7-Amino-4-Trifluoromethylcourmarin", *Thrombosis Res.*, vol. 17, (1980), pp. 393–402.
Hine, *Structural Effects on Equilibria in Organic Chemistry*, John Wiley & Sons, N. Y. (1975), pp. 44, 92, 161.

*Primary Examiner*—Thomas G. Wiseman
*Attorney, Agent, or Firm*—Edward A. Figg; Donald L. Barbeau

[57] ABSTRACT

A method is disclosed for determining the presence of an enzyme in a biological fluid, which includes the steps of contacting the fluid with a synthetic chromogenic substrate, which is an amino acid derivative of 7-amino-4-trifluoromethylcoumarin; incubating the substrate-containing fluid to effect enzymatic hydrolysis; and fluorometrically determining the presence of the free 7-amino-4-trifluoromethylcoumarin chromophore in the hydrolyzate.

14 Claims, No Drawings

SUBSTRATES AND METHOD FOR DETERMINING ENZYMES

The government has rights in this invention pursuant to Contract No. W-7405-ENG-48 awarded by the U.S. Department of Energy.

BACKGROUND OF THE INVENTION

The present invention relates to substrates and methods for determining enzymes. More particularly, the invention relates to qualitative and quantitative methods for determining proteolytic enzymes.

The determination of specific enzymes in biological fluids, such as blood, tissue homogenates, and cytoplasm can be very useful for the diagnosis of certain diseases. The discovery of synthetic substrates for such determinations has resulted in clinical assay procedures having a high degree of specificity, reliability, and sensitivity. Such substrates have been employed for the determination of amylase (Driscoll, R. C., et al., U.S. Pat. No. 4,102,747) and various proteinases.

Synthetic proteinase substrates have generally been amino acid derivatives of aromatic amines. The number and arrangement of amino acids in the peptide moiety determine the enzyme specificity of the substrate and the enzyme activity is measured by the amount of aromatic amine moiety liberated upon hydrolysis of the substrate. Amino acid derivatives of p-nitroaniline have been widely used as synthetic substrates. Erlanger, B. F., U.S. Pat. No. 3,412,150. Other aromatic amines which have been reacted with amino acids or peptides include 2-naphthylamine, 4-methoxy-2-naphthylamine, and 7-amino-4-methylcoumarin. The use of 2-naphthylamine and 4-methoxy-2-naphthylamine for the preparation of synthetic substrates and prior art relating thereto are discussed by Smith, R. E., U.S. Pat. No. 3,862,011. Peptide derivatives of 7-amino-4-methylcoumarin have recently been reported as fluorogenic substrates for a number of proteinases. Zimmerman, M., Yurewicz, E., Patel, G., *Anal. Biochem.* 70, 258–262 (1976) and Zimmerman, M., Quigley, J. P., Ashe, B., Dorn, C., Goldfarb, R., Troll, W., *Proc. Natl. Acad. Sci.*, 75, 750–753 (1978).

Because the chromophore, p-nitroaniline, is yellow, enzyme assays employing that chromophore are colorimetric. Fluorescence assays are sometimes preferred over colorimetric assays, because of greater sensitivity and less background interference. The aromatic amine chromophores heretofore used to prepare synthetic substrates are fluorescent, but their fluorescence generally occurs in the blue region of the spectrum. Such fluorescence is disadvantageous, because it is difficult to measure with inexpensive instruments, and it is similar to fluorescense of other materials present in the analyte, including, in some instances, the intact substrate. These assays are useful for cytological studies for the detection of an enzyme within a single cell. When such cells are viewed under a fluorescence microscope, a blue color is difficult to see or distinguish from the background, but cells emitting light in the yellow region of the spectrum are easily visualized.

To overcome these problems, investigators have focused on reactions involving the enzyme-liberated chromophore to enhance color or fluorescence at a desired wavelength. For instance, aromatic amine chromophores may be reacted with diazonium salts to from azo dyes which are determined spectrophotometrically. In U.S. Pat. No. 4,155,916, R. E. Smith, et al. disclose a reaction of the aromatic amine chromophore with certain aromatic aldehydes to from Shiff base compounds which fluoresce in the yellow-green region of the spectrum.

Although such methods have each constituted significant advances over the prior art, there is a need for synthetic substrates for proteinase enzymes which do not fluoresce in the yellow region, but which upon enzyme hydrolysis, release a chromophore which fluoresces strongly in that region of the spectrum. Such substrates would, thus, obviate the need for further reactions involving the liberated chromophore, and the concentration of such chromophore could be readily determined by a fluorometric technique.

SUMMARY OF THE INVENTION

In accordance with the present invention, there is disclosed a method for determining the presence of an enzyme in an enzyme-containing analyte, comprising:

(a) contacting the analyte with a substrate which can be hydrolyzed by said enzyme to liberate 7-amino-4-trifluoromethylcoumarin, said substrate having the formula

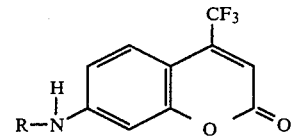

wherein R is an amino acid, a peptide, or a derivative thereof, thereby forming an analyte-substrate mixture;

(b) incubating the analyte-substrate mixture under enzyme hydrolyzing conditions to form an enzyme hydrolyzate; and (c) fluorometrically or spectrophotometrically determining the presence of 7-amino-4-trifluoromethylcoumarin in the enzyme hydrolyzate.

DETAILED DESCRIPTION OF THE INVENTION

The substrates of the present invention are represented by the formula

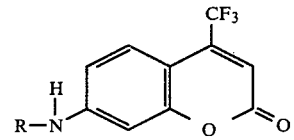

wherein R may be a single amino acid or a peptide, consisting of two or more amino acids. The terminal amino acid may be reacted with any suitable blocking groups as is well known in the art, such as carbobenzoxy, benzoyl, glutaryl, t-butyloxycarbonyl, and certain d-amino acids, e.g. d-proline, d-valine, or d-alanine.

Thus, upon enzymatic hydrolysis, the chromophore, 7-amino-4-trifluoromethylcoumarin is released. This chromophore fluoresces strongly in the yellow region of the spectrum when irradiated with ultraviolet light, but the intact substrates fluoresce very weakly, if at all, in that region. The fluorescent properties of the substrates and the chromophore render these compounds particularly useful for the enzyme assays. The presence of the liberated substrate can be qualitatively or quantitatively determined fluorometrically without employing dye-forming or wavelength-shifting reactions.

In contrast with prior art substrates which are used either in colorimetric or fluorometric assays, but not both, the present substrates may be used in both direct colorimetric and fluorometric assays. The 7-amino-4-trifluoromethylcoumarin chromophore has a yellow color, but the intact substrates are substantially colorless. Thus, the substrates can be employed in spectrophotometric as well as fluorometric assays. This property of the substrates makes them particularly valuable for use in enzyme kinetic studies.

The number and arrangement of amino acids attached to the chromophore determine the enzyme specificity for the substrate. Any combination of amino acids can be employed to obtain the desired specificity. Preferably, the amino acid chain consists of from 1 to about 12 amino acids and, most preferably from 1 to about 6 amino acids. The amino acids are bound together through peptide bonds.

Advantageously, the amino acid chain may be terminated with a blocking group. Such a blocking group may be employed during the synthesis of the substrate to prevent reactions with the terminal amino acid, and the blocking group is sometimes employed in substrates to improve enzyme specificity. Such blocking groups are well known in the art as described above.

Preferred substrates of the present invention are compounds represented by the above formula wherein R is Cbz-Gly-Gly-Arg-; D-Ala-Leu-Lys-; Cbz-Val-Lys-Lys-Arg- and Leu- (Cbz represents carbobenzoxy and the amino acid abbreviations are generally recognized and accepted in the art). The first substrate is useful for assays for trypsin and urokinase, the second is useful for plasmin assays, the third is useful for the determination of cathepsin B, and the fourth is useful for the determination of aminopeptidase M.

The substrates may be prepared by acylating 7-amino-4-trifluoromethylcoumarin with an appropriate amino acid or peptide. Such acylation may be accomplished by a conventional mixed anhydride reaction. Similarly, amino acids or peptides can be added to substrates having one or more unblocked amino acids. For instance, a urokinase substrate can be prepared by the following reaction scheme:

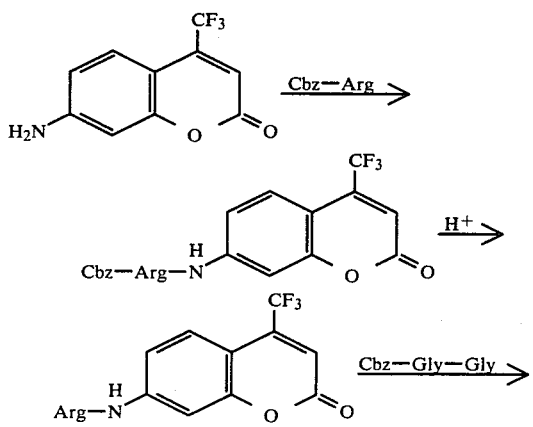

-continued

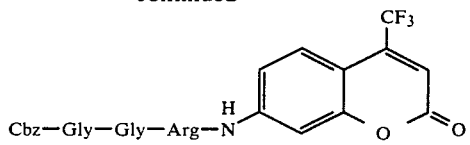

Any desired number and arrangement of amino acids may thus be added onto the chromophore. Blocking groups may be removed, e.g. by hydrogenolysis or treatment with anydrous hydrogen bromide in acetic acid, trifluoroacetic acid or other conventional deblocking agents as are known in the art.

In the practice of the method of the present invention, an analyte containing, or suspected of containing, an enzyme is contacted with a substrate which can be hydrolyzed by that enzyme. Such analyte is usually a natural biological fluid such as blood, serum, urine, tissue homogenate, etc., but may also be a synthetic solution used for quality control or as a reference standard. The substrate is generally employed in excess of the amount which can be completely hydrolyzed by the quantity of enzyme present. For instance, the substrate is preferably employed in an amount of from 1 to about 10 times, most preferably from about 1 to about 4 times that amount which can be completely hydrolyzed by the enzyme.

The analyte-substrate mixture is incubated under enzyme-hydrolyzing conditions to form an enzyme hydrolyzate. Such enzyme-hydrolyzing conditions include conditions of pH and temperature which are conducive to the enzymatic hydrolysis of the substrate. The pH of the analyte-substrate mixture will generally be in the range of the normal physiological evironment of the enzyme, and thus may vary from one enzyme to another. Such pH is usually in a range of from about 4 to about 10, and preferably in a range of from about 5 to about 8.5. A pH of about 8 has been employed for urokinase, plasmin, and trypsin assays and a pH of about 7.2 has been used for aminopeptidase M assays. The pH of the mixture is conveniently controlled by dissolving the analyte and substrate in an appropriate buffer, as is well known in the art. A suitable buffer is N-tris(hydroxymethyl)methyl-2-aminoethanesulfonic acid (TES).

The temperature at which the enzyme hydrolysis is effected is not critical, and may fall within a broad range, provided that the temperature is high enough to insure enzyme activity, but not too high to cause degradation or other deleterious reactions involving the substrate, the enzyme, or other components of the mixture. The temperature advantageously is from about 15° C. to about 50° C., preferably from about 20° C. to about 40° C.

The fluorometric determinaton of the liberated chromophore may be either a rate determination or an endpoint determination. Rate determinations are preferred, because they are generally more sensitive and precise. In a rate determination, the fluorescence of the substrate-analyte mixture may be determined promptly after the analyte is contacted with the substrate. In an endpoint determination, the enzyme hydrolysis reaction is allowed to proceed for a predetermined length of time, e.g. from about 5 to about 60 minutes, preferably from about 15 to about 30 minutes. Such reaction time is selected so that a sufficient quantity of chromophore has been released to provide an acceptable degree of accuracy for the assay.

For fluorometric assays, excitation and emission wavelengths may be selected to conform to existing equipment commonly available in clinical laboratories. Maximum excitation and emission wavelengths for the 7-amino-4-trifluoromethylcoumarin chromophore are 365 nm and 495 nm, respectively. Wavelengths of 400 nm and 505 nm have been employed; and at these wavelengths, the fluorescence of the liberated chromophore is about 700 times greater than an equimolar solution of the substrate, while retaining about 57% of the maximum fluorescence.

The absorbance maximum wavelength for the liberated chromophore is about 370 nm. In spectrophotometric assays, the absorbance measurements are usually made at about 380 nm to minimize interference by the intact substrate.

Those skilled in the art will recognize that the substrates of this invention may be useful in a variety of analytical techniques. For instance, the substrates can be utilized in cytological studies to indicate the presence of certain enzymes in single cells. Other uses of the substrates include their utilization as indicators for various chromatographic or electrophoretic techniques. Enzymes may be isolate by chromatography, e.g. paper chromatography, thin-layer chromatography or column chromatography, or by electrophoresis and the appropriate substrate may be applied to the chromatographic or electrophoretic medium to indicate the location or intensity of the enzyme spot, band, or zone.

Thus, there has been discovered a sensitive and reliable method and novel substrates for the determination of proteinase enzymes.

The invention is further illustrated by the following examples which are not intended to be limiting.

EXAMPLE I

This example describes a procedure for preparing a substrate of the formula

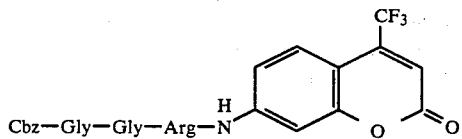

wherein Cbz is carbobenzoxy, and is applicable to the preparation of any of the substrates of the present invention by selection of the proper reactants.

Cbz-arginine, 1.7 g, was dissolved in 10 ml of dry dimethylformamide, the solution was cooled in an ice-actone bath, and 0.75 ml of isoamylchloroformate was added. The mixture was stirred for three hours at −15° C. 7-amino-4-trifluoromethylcoumarin, 1.15 g, was added and stirring was continued for another 20 hours while the bath was allowed to warm to room temperature. The solvents were removed by vacuum distillation at 5 mm Hg pressure at room temperature, and the residue was dried overnight under 10μ of Hg pressure at room temperature. The crude reaction mixture was purified by high performance liquid chromatography using a silica gel column and 10% methanol in methylenedichloride as the eluant, thus yielding a product of the formula:

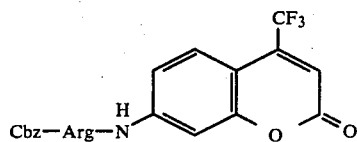

That product, 555 mg, was dissolved in 5 ml of 32% HBr in acetic acid. After 30 minutes at room temperature, the orange solution was poured into 80 ml of ether. The mixture was centrifuged and the precipitate was washed twice with ether and dried overnight. This procedure is effective for removing the carbobenzoxy blocking group. The resulting product, 0.98 g, was dissolved in 5.0 ml of dry dimethylformamide, and this solution was combined with the mixed anydydride prepared from 660 mg of Cbz-Gly-Gly in 5.0 ml of dried dimethylformamide at −15° C. (mixed anyhdride prepared by reacting Cbz-Gly-Gly with isobutylchloroformate in the presence of N-methylmorpholine in DMF solvent). The mixture was stirred overnight as the temperature was allowed to reach room temperature. The solvents were removed by vacuum distillation at 5 mm Hg pressure at room temperature, and the residue was dried overnight at room temperature at 30μ Hg pressure. The product was purified by twice subjecting it to high pressure liquid chromatography on a silica gel column using 20% methanol in methylenedichloride. The nuclear magnetic resonance spectrum of the product was consistent with the assigned structure. The optical rotation of the product (195 mg/10 ml methanol) $[\alpha]_D^{23} -6.4°$. The elemental analysis for carbon, hydrogen, and nitrogen was also consistent with the assigned structure.

EXAMPLE II

A series of experiments was conducted to demonstrate the method of the present invention. Solutions of each of the enzymes, urokinase, plasmin, aminopeptidase M, and trypsin were prepared at various concentrations within the ranges indicated in Table I. For trypsin and urokinase assays, the substrate cbz-gly-gly-arg-7-amino-4-trifluoromethylcoumarin was used as the substrate. For plasmin assays, d-ala-leu-lys-7-amino-4-trifluoromethylcoumarin was used, and for aminopeptidase M assays, leu-7-amino-4-trifluoromethylcoumarin was used. Dimethylformamide solutions of the substrates ($10^2$ millimolar for aminopeptidase M assays and 20 millimolar for trypsin, urokinase, and plasmin assays) were prepared. To conduct an assay, 50 μl of substrate solution was added to 900 μl of buffer (0.05 M TES, pH 8, for urokinase and plasmin; 0.05 M TES, pH 7.2, for aminopeptidase M; 0.5 M TES, pH 8.0 for trypsin) in a cuvette. To this solution, 50 μl enzyme solution was added and the temperature was controlled at 25° C. Fluorescence was recorded for five minutes or more on a recording spectrofluorometer using an excitation wavelength of 400 nm and an emission wavelength of 505 nm. The rate of increase of fluorescence was linear over the enzyme concentration ranges indicated in Table I, and the rate of increase of fluorescence was found to be directly proportional to enzyme concentration.

TABLE I

| Enzyme | Substrate C=7-amino-4-trifluoro-methylcoumarin | Linear Range | Detection Limit |
| --- | --- | --- | --- |
| Trypsin | Cbz—Gly—Gly—Arg—C | 0.08–25 ng/ml | 0.08 ng/ml |
| Urokinase | Cbz—Gly—Gly—Arg—C | 0.75–50 I.U./ml | 0.75 I.U./ml |
| Plasmin | d—Ala—Leu—Lys—C | 0.0006–0.06 CTA/ml | 0.0006 CTA/ml |
| Aminopeptidase M | Leu—C | 6.0–600 ng/ml | 6.0 ng/ml |

EXAMPLE III

A patient serum may be assayed for the enzyme cathepsin B by the following procedure. A 2 millimolar solution of the substrate Cbz-Val-Lys-Lys-Arg-7-amino-4-trifluoromethylcoumarin in dry dimethylformamide was prepared. This substrate solution, 50 μl, was added to 900 μl of 0.05 sodium cacodylate buffer (pH 5.6–6.2) in a cuvette. To this solution, 50 μl of 1:10 diluted patient serum was added and the temperature was controlled at 25° C. Fluorescence was measured as described in Example II and the rate of increase of fluorescence was compared to a standard calibration curve to determine enzyme concentration.

We claim:

1. A method for determining the presence of an enzyme in an enzyme-containing analyte, comprising:
   (a) contacting the analyte with a substrate which can be hydrolyzed by said enzyme to liberate 7-amino-4-trifluoromethylcoumarin, said substrate having the formula

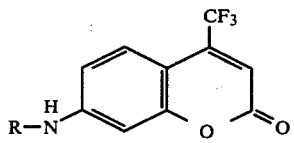

wherein R is an amino acid, a peptide, an amino acid which has been reacted with a blocking group, or a peptide, the terminal amino acid of which has been reacted with a blocking group, thereby forming an analyte-substrate mixture;
   (b) incubating the analyte-substrate mixture under enzyme-hydrolyzing conditions to form an enzyme hydrolyzate; and
   (c) fluorometrically or spectrophotometrically determining the presence of 7-amino-4-trifluoromethylcoumarin in the enzyme hydrolyzate.

2. The method of claim 1, wherein R is an amino acid chain comprising from 1 to about 12 amino acids.

3. The method of claim 1, wherin R is an amino acid chain comprising from 1 to about 6 amino acids.

4. The method of claim 1, wherein R is gly-gly-arg-.

5. The method of claim 1, wherein R is d-ala-leu-lys-.

6. The method of claim 1, wherein R is leu-.

7. The method of claim 1, werein R is Cbz-Val-Lys-Lys-Arg-.

8. The method of any one of claims 2, 3, 4, 5, 6, or 7, wherein said blocking group is carbobenzoxy, benzoyl, glutaryl, t-butyloxycarbonyl, d-proline, d-valine or d-alanine.

9. The method of claim 1, wherein said enzyme-hydrolyzing conditions include a pH of from about 4 to about 10 and a temperature of from about 15° C. to about 50° C.

10. The method of claim 1, wherein said enzyme-hydrolyzing conditions include a pH of from about 5 to about 8.5 and a temperature of from about 20° C. to about 40° C.

11. The method of claim 9, wherein the determination is a fluorometric rate determination and employs an excitation wavelength of about 400 nm and an emission wavelength of about 505 nm.

12. The method of claim 9 wherein the determination is spectrophotometric and absorbance measurements are made at about 380 nm.

13. The method of claim 9, 10, 11, or 12 wherein the analyte is a biological fluid and the enzyme is a proteinase enzyme.

14. The method of claim 13, wherein the biological fluid is the cytoplasm within a single cell.